(12) United States Patent
Petti et al.

(10) Patent No.: US 10,357,466 B2
(45) Date of Patent: Jul. 23, 2019

(54) COMPOSITIONS AND METHODS FOR COMBINATION PHARMACOLOGICAL TREATMENTS TO INDUCE A PROLONGED, MILD DECREASE IN CORE BODY TEMPERATURE

(71) Applicants: Stephen J. Petti, Troy, NY (US); Samn Raffaniello Petti, Troy, NY (US)

(72) Inventors: Stephen J. Petti, Troy, NY (US); Samn Raffaniello Petti, Troy, NY (US)

( * ) Notice: Subject to any disclaimer, the term of this patent is extended or adjusted under 35 U.S.C. 154(b) by 0 days.

(21) Appl. No.: 15/224,725

(22) Filed: Aug. 1, 2016

(65) Prior Publication Data
US 2017/0027892 A1    Feb. 2, 2017

Related U.S. Application Data

(60) Provisional application No. 62/200,004, filed on Aug. 1, 2015.

(51) Int. Cl.
| | |
|---|---|
| *A61K 45/06* | (2006.01) |
| *A61P 43/00* | (2006.01) |
| *A61K 31/155* | (2006.01) |
| *A61K 31/436* | (2006.01) |
| *A61K 31/551* | (2006.01) |
| *A61K 31/475* | (2006.01) |
| *A61K 31/519* | (2006.01) |
| *A61K 31/4745* | (2006.01) |
| *A61K 31/5513* | (2006.01) |

(52) U.S. Cl.
CPC .......... *A61K 31/155* (2013.01); *A61K 31/436* (2013.01); *A61K 31/475* (2013.01); *A61K 31/4745* (2013.01); *A61K 31/519* (2013.01); *A61K 31/551* (2013.01); *A61K 31/5513* (2013.01); *A61K 45/06* (2013.01); *A61P 43/00* (2018.01)

(58) Field of Classification Search
CPC .............. A61K 31/155; A61K 31/4745; A61K 31/519; A61K 31/5513; A61K 45/06
USPC ...................................................... 514/1, 22
See application file for complete search history.

(56) References Cited

U.S. PATENT DOCUMENTS

| | | | |
|---|---|---|---|
| 6,194,466 B1 * | 2/2001 | Cottingham | A61K 31/155 514/557 |
| 8,138,169 B2 * | 3/2012 | Oronsky | A61K 31/485 514/211.13 |
| 8,969,297 B2 | 3/2015 | Katz | |
| 9,757,431 B2 | 9/2017 | Katz | |
| 2003/0131844 A1 | 7/2003 | Kumar et al. | |
| 2004/0102368 A1 | 5/2004 | Katz | |
| 2008/0044390 A1 * | 2/2008 | Jin | A61K 31/155 424/93.7 |
| 2009/0311347 A1 | 12/2009 | Oronsky et al. | |
| 2010/0092549 A1 * | 4/2010 | Blundell | A61K 9/2072 424/456 |
| 2012/0282227 A1 | 11/2012 | Katz | |
| 2013/0116215 A1 * | 5/2013 | Coma | A61K 31/165 514/108 |
| 2014/0350064 A1 * | 11/2014 | Chen | A61K 31/137 514/415 |

FOREIGN PATENT DOCUMENTS

| | | |
|---|---|---|
| WO | 2009071097 A1 | 6/2009 |
| WO | 2017023833 A1 | 2/2017 |

OTHER PUBLICATIONS

Boyda et al., "Antidiabetic-drug combination treatment for glucose intolerance in adult female rats treated acutely with olanzapine", Jan. 2014, Progress in Neuro-Psychopharmacology & Biological Psychiatry, 48, pp. 170-176. (Year: 2014).*
Mendelsohn et al., "Rapamycin as an Antiaging Therapeutic?: Targeting Mammalian Target of Rapamycin to Treat Hutchinson—Gilford Progeria and Neurodegenerative Diseases", 2011, Rejuvenation Research, 14(4), pp. 437-441. (Year: 2011).*
Osorio et al., "Splicing-Directed Therapy in a New Mouse Model of Human Accelerated Aging", 2011, Science Translational Medicine, 3(106), pp. 1-11 (DOI: 10.1126/scitranslmed.3002847) (Year: 2011).*
Lopez-Otin et al., "The Hallmarks of Aging", 2013, Cell, 153(6), pp. 1194-1217. (Year: 2013).*
Carrero et al., "Hallmarks of progeroid syndromes: lessons from mice and reprogrammed cells", 2016, Disease Models & Mechanisms, 9(7), pp. 719-735. (Year: 2016).*
Rasnayake et al. "An Unusual Case of Hypothermia Associated with Therapeutic Doses of Olanzapine: a Case Report", Journal of Medical Case Reports, vol. 5 No. 189, 2011, pp. 1-4.
Wikipedia "Metformin" last updated Jul. 29, 2015, cited in the Nov. 29, 2016 ISR of International App. No. PCT/US16/44961. Retrieved from the Internet at https://en.wikipedia.org/w/index.php?title=Metformin&oldid=673658664 on Aug. 28, 2018.

(Continued)

*Primary Examiner* — My-Chau T. Tran
(74) *Attorney, Agent, or Firm* — Heslin Rothenberg Farley & Mesiti P.C.

(57) ABSTRACT

The present invention is directed to combination pharmacological treatments that induce a prolonged, modest decrease in core body temperature, to the range of ~95° F. to ~98.5° F. (~35° C. to ~36.7° C.) to mitigate and delay the early onset and progression of fatal disease processes associated with premature aging, such as those characteristic of progeria (Hutchinson-Gilford Progeria Syndrome, HGPS), Wiedemann-Rautenstrauch syndrome (neonatal progeroid syndrome), Werner syndrome, and other rare disorders characterized by premature aging, and to prolong the shortened lifespan of children afflicted with these diseases. Short-term chronic administration of the pharmaceutical treatments to a person suffering from mild concussion may also have value in ameliorating neurological damage/symptoms associated with mild concussion. Chronic administration of the pharmacological treatments may also have value in normal human populations or in high-risk human populations. Similar benefits may be realized in other mammals such as canines, felines and other non-human species.

9 Claims, 3 Drawing Sheets

(56) References Cited

OTHER PUBLICATIONS

Wikipedia "Reserpine" last updated Jun. 28, 2015, cited in the Nov. 29, 2016 ISR of International App. No. PCT/US16/44961. Retrieved from the Internet at https://en.wikipedia.org/w/index.php?title=Reserpine&oldid=669083766 on Aug. 28, 2018.
Wikipedia "Anti-diabetic medication" last updated Jul. 22, 2015, cited in the Nov. 29, 2016 ISR of International App. No. PCT/US16/44961. Retrieved from the Internet at https://en.wikipedia.org/w/index.php?title=Anti-diabetic_medication&oldid=672650810 on Aug. 28, 2018.
Wikipedia "Chronotherapy (treatment scheduling)" last updated Jan. 1, 2015, cited in the Nov. 29, 2016 ISR of International App. No. PCT/US16/44961. Retrieved from the Internet at https://en.wikipedia.org/w/index.php?title=Chronotherapy_(treatment_scheduling)&oldid=640538765 on Aug. 28, 2018.
Wikipedia "Circadian rhythm" last updated Aug. 27, 2018, cited in the Nov. 29, 2016 ISR of International App. No. PCT/US16/44961. Retrieved from the Internet at https://en.wikipedia.org/w/index.php?title=Circadian_rhythm&oldid=669957213 on Aug. 28, 2018.
University of Michigan "Old drug may point the way to new treatments for diabetes and obesity" ScienceDaily, Feb. 10, 2013, cited in the Nov. 29, 2016 ISR of International App. No. PCT/US16/44961. Retrieved from the Internet at https://www.sciencedaily.com/releases/2013/02/130210143250.htm on Aug. 28, 2018.
Hu et al. "Metformin and Berberin Prevent Olanzapine-Induced Weight Gain in Rats", PLOS One, vol. 9, No. 3, pp. 1-9, Mar. 25, 2014.
Evers et al. "Olanzapine Causes Hypothermia, Inactivity, a Deranged Feeding Pattern and Weight Gain in Female Wistar Rats" Pharmacology, Biochemistry and Behavior, vol. 97, No. 1, Nov. 2010, pp. 163-169.
Baptista et al. "Metformin as an Adjunctive Treatment to Control Body Weight and Metabolic Dysfunction During Olanzapine Administration: A Multicentric, Double-Blind, Placebo-Controlled Trial" ScienceDirect, Schizophrenia Research, vol. 93, Mar. 20, 2007, pp. 99-108.
Baptista et al. "Metformin for PRevention of Weight Gain and Insulin Resistance with Olanzapine: A Double-Blind Placebo-Controlled Trial" Can. J. Psychiatry, vol. 51, No. 3, Mar. 2006, pp. 192-196.
Metformin Package Insert "Glucophage (metformin hydrochloride) Tables" Distributed by Bristol-Myers Squibb Company, revised Apr. 2017.
Zyprexa Package Insert "Highlights of Prescribing Information" Lilly USA, LLC, last revised Jan. 19, 2018.
Asanka De Silva et al. "Metformin in Prevention and Treatment of Antipsychotic Induced Weight Gain: a Systematic Review and Meta-Analysis" BMC Psychiatry, 2016, pp. 1-10.
International Search Report of International App. No. PCT/US16/44961, dated Nov. 29, 2016.
Written Opinion of the International Searching Authority for International App. No. PCT/US16/44961, dated Nov. 29, 2016.
Esmat Mustafa, MD et al. "Rapid Recovery from Acute Kidney Injury in a Patient with Metformin-associated Lactic Acidosis and Hypothermia", The American Journal of Medicine, vol. 125, No. 2, pp. e1-e2. Feb. 2012.
Por-Wen Yang et al., "Sucessful Treatment of Severe Lactic Acidosis Caused by a Suicide Attempt with a Metformin Overdose", Kaohsiung J. Med Sci, vol. 25, No. 2, pp. 93-97. Feb. 2009.
Extended European Search Report in European Application No. 16833666.7, dated Feb. 18, 2019.

* cited by examiner

Figure 1. Correlations between longevity and body temperature, insulin levels, and DHEAS levels.

Source: Roth *et al.* (2002) *Science* 297, 811.

Figure 2. Survival and mortality curves.

Source: Conti *et al.* (2006) *Science* 314, 825-828.

Figure 3. Mean body temperature (°F) by age and gender.

| Age Group (years) | Women | | Men | |
|---|---|---|---|---|
| | *N* | *M (SD)* | *N* | *M (SD)* |
| 20-29 | 210 | 97.70 (1.08) | 162 | 97.28 (0.99) |
| 30-39 | 729 | 97.77 (1.11) | 617 | 97.25 (1.13) |
| 40-49 | 1,724 | 97.73 (1.15) | 1,571 | 97.26 (1.28) |
| 50-59 | 2,316 | 97.45 (1.12)* | 2,482 | 97.20 (1.07) |
| 60-69 | 2,403 | 97.31 (1.17)* | 2,458 | 97.11 (1.08) |
| 70-79 | 1,505 | 97.32 (1.14)* | 1,691 | 97.06 (1.09)* |
| 80+ | 339 | 97.36 (1.30)* | 422 | 97.01 (1.13)* |

*$p < 0.05$ compared with youngest age group (20-29 years) of the same sex, corrected with Dunnett's test for multiple comparisons.

Source: Waalen & Buxbaum (2011) *J. Gerontol. A Biol. Sci. Med. Sci.* 66A, 487-492.

COMPOSITIONS AND METHODS FOR COMBINATION PHARMACOLOGICAL TREATMENTS TO INDUCE A PROLONGED, MILD DECREASE IN CORE BODY TEMPERATURE

CROSS-REFERENCE TO RELATED APPLICATIONS

This application claims benefit under 35 U.S.C. § 119(e) of U.S. Patent Application No. 62/200,004, filed Aug. 1, 2015, which is hereby incorporated herein by reference in its entirety.

BACKGROUND TO THE INVENTION

Hypothermia

The Baltimore Longitudinal Study of Aging (BLSA)

In the Baltimore Longitudinal Study of Aging (BLSA), men with core body temperatures below the median lived significantly longer than men with body temperatures above the median, in the absence of caloric restriction (CR). The BLSA has accumulated almost 30 years of follow-up data in a large population and continues today (Roth et al. (2002) *Science* 297, 811).

Specifically, in the largest reported longitudinal study of body temperature in humans, it was reported, a decade ago, in men in the BLSA study that participants with core body temperatures in the lower 50% of the study population had significantly lower mortality than those with body temperatures in the upper 50% over 25 years of follow-up (Soare et al. (2011) *Aging* 3, 374-379).

In humans the average internal temperature is generally considered to be ~37.0° C. (~98.6° F.), although it varies among individuals. Roth et al. examined the effects of various longevity-related markers from the BLSA. Consistent with the beneficial effects of caloric restriction on aging and lifespan in other animals, men with lower temperatures had greater survival than those with higher temperatures, but the BLSA men were not calorie-restricted.

Figure 1:
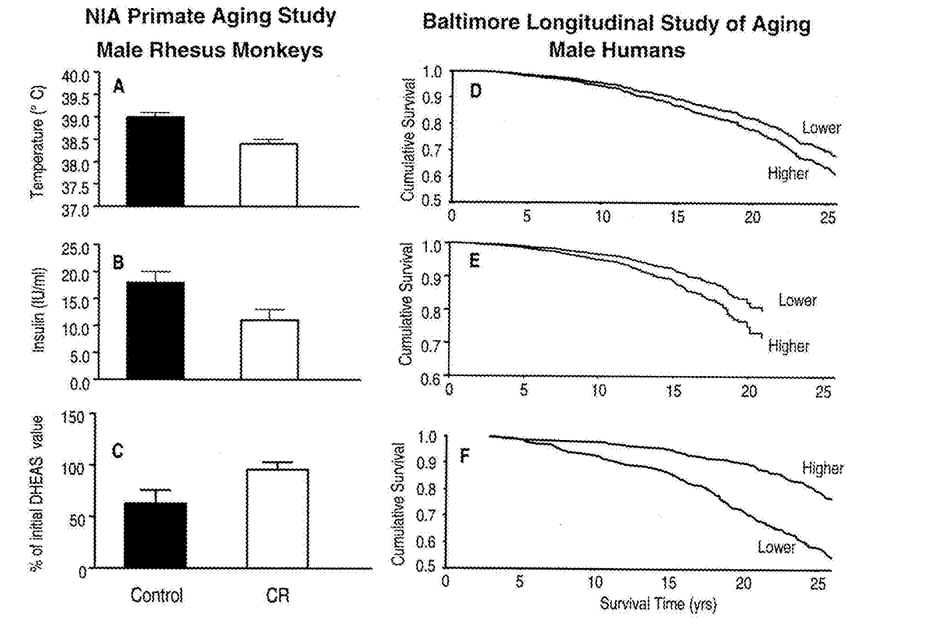
FIG. 1. Correlations between longevity and body temperature, insulin levels, and DHEAS levels.
Figure 2:
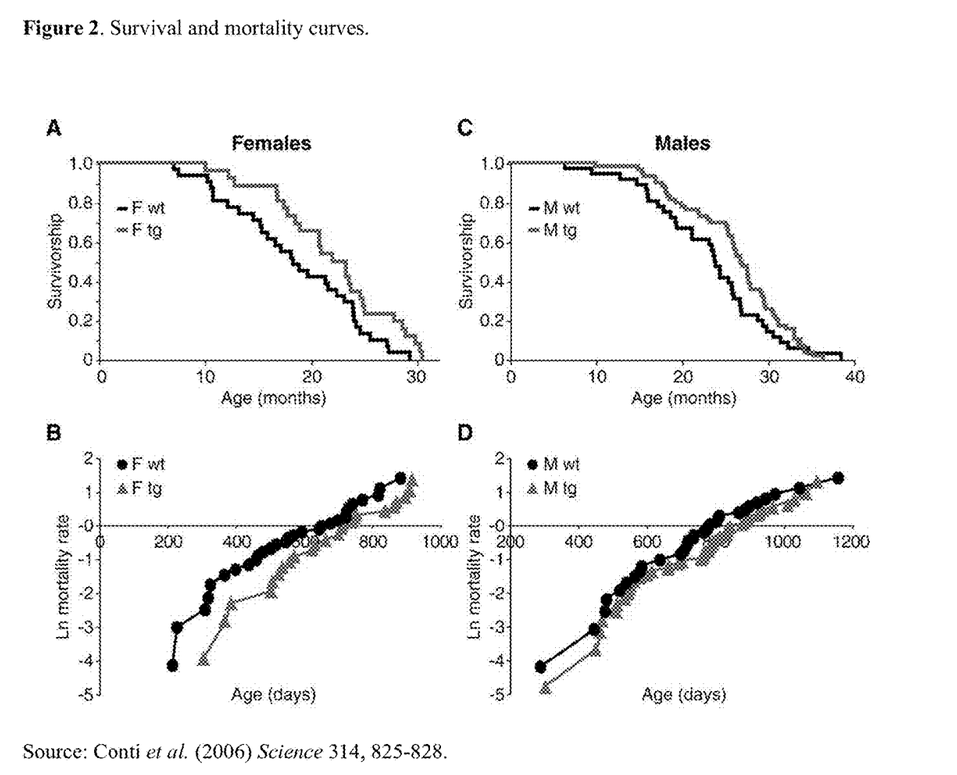
FIG. 2. Survival and mortality curves.
Figure 3:
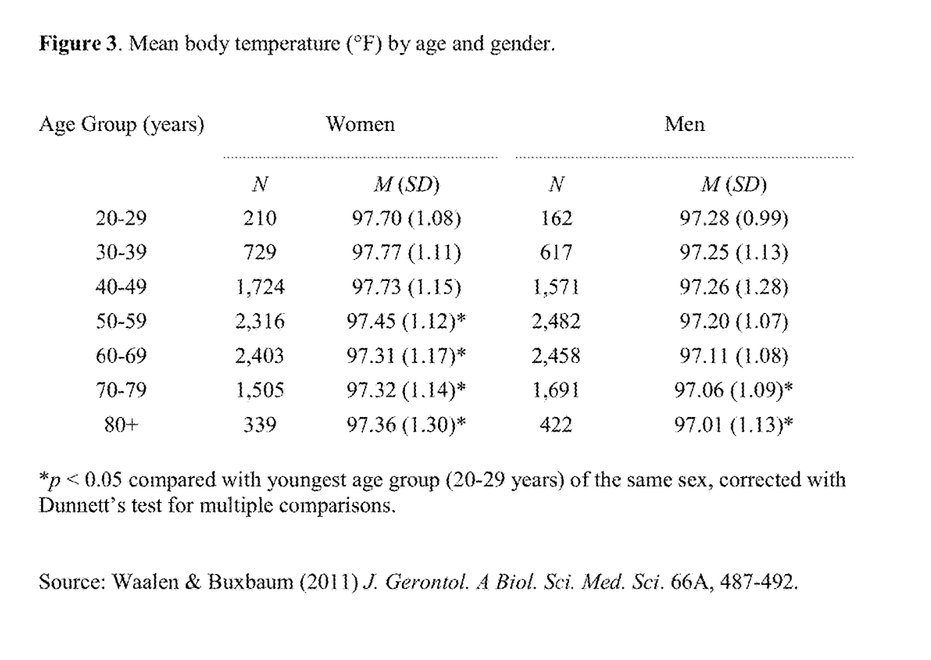
FIG. 3. Mean body temperature by age and gender.

Furthermore, lower body temperature was reported to be one of only three independent factors influencing longevity (FIG. 1).

The Scripps Research Institute Study

In a 2006 study, scientists at the Scripps Research Institute found that reducing the core body temperature of mice extended their median lifespan, by up to 20% (Conti et al. (2006) *Science* 314, 825-828). This was the first time that changes in body temperature had been shown to affect lifespan in warm-blooded animals. The study demonstrated that it was possible to increase lifespan in mice by modest, but prolonged, lowering of the core body temperature and that the longer lifespan was achieved independent of caloric restriction.

Prior to this study, researchers had known that core body temperature and aging were related in cold-blooded animals. Scientists had also known that lifespan could be extended in warm-blooded animals by reducing the number of calories they consumed, which also lowered core body temperature as a consequence. However, the degree of caloric restriction needed to extend lifespan is not easy to achieve, even in mice.

Prior to the Scripps study, key questions about the relationship between caloric restriction, core body temperature, and lifespan remained unanswered. Was caloric restriction itself responsible for longer lifespan, with reduced body temperature simply a consequence? Or was the reduction of core body temperature a key contributor to the beneficial effects of caloric restriction?

Mice in the Scripps study were allowed to eat as much food as they wished, and the experimental and control mice ate the same amount suggesting that hypothermia—and not caloric restriction—may be more directly tied to longevity (Conti et al. (2006) *Science* 314, 825-828). Other examples illustrating and supporting this point follow.

The Naked Mole Rat

Another example of a lower body temperature's effects on aging is the naked mole rat (*Heterocephalus glaber*), a subterranean, extraordinarily long-lived eusocial mammal (Kim et al. (2011) *Nature* 479, 223-227). Although the size of a mouse, the naked mole rat's maximum lifespan exceeds 30 years and makes this animal by far the longest living rodent (~10 times the typical lifespan of comparably sized rodents).

Naked mole rats show negligible senescence, no age-related increase in mortality, and high fecundity until death. In addition to delayed aging, naked mole rats are resistant to both spontaneous cancer and experimentally induced tumorigenesis. They also maintain healthy vascular function longer in their lifespan than shorter-lived rats. The naked mole rat's normal core body temperature is a full 6° C. lower than any other rodent.

It was at first considered that the naked mole rat's exceptional lifespan was associated with its burrowing lifestyle that included intermittent periods of 'feast' and prolonged 'famine' (calorie restriction). However, the precise reason for their longevity is still debated and is likely the result of many factors.

Longevity was thought to be related to the naked mole rat's ability to substantially reduce its metabolism during hard times, and so to prevent aging-induced damage from oxidative stress. However, when naked mole rats were removed to captivity, they survived to their full potential and remained resistant to disease whether fed their native diet in a feast-famine pattern or a full ad libitum diet, ingested at will. Their core body temperatures, however, remained low. As noted with the Scripps study, the suggestion was that hypothermia—and not caloric restriction—may be more directly tied to the naked mole rat's resistance to disease and remarkable longevity.

Progeria and Progeria-Like Diseases in Children

Progeria, also known as Hutchinson-Gilford Progeria Syndrome (HGPS), is a rare, fatal genetic condition of accelerated aging in children (Gordon et al. (2012) *J. Cell Biol.* 199, 9-13). All children with progeria die of the same heart disease that affects millions of normally aging adults (arteriosclerosis), but instead of this occurring at 60-70 years of age, the children may suffer strokes and heart attacks even before age 10.

Progeria affects ~1 in 4-8 million newborns. There are an estimated 200-250 children living with Progeria worldwide at any one time. It affects both sexes equally and all races (Sarkar & Shinton (2001) *Postgrad. Med J.* 77, 312-317).

Progeria is a progressive genetic disorder that causes children to age rapidly, beginning in their first 2 years of life. Children with progeria generally appear normal at birth. By 12 months, signs and symptoms, such as slow growth and hair loss, begin to appear. The average life expectancy for a child with progeria is ~13, but some with the disease die younger and some live 20 years or longer.

Heart problems or strokes are the eventual cause of death in most children with progeria. There is currently no treatment for the condition.

Researchers have discovered a single gene mutation responsible for HGPS. The gene is known as lamin A (LMNA), which encodes a protein necessary for holding the nucleus of a cell together. It is believed that the genetic mutation renders cells unstable, which appears to lead to progeria's characteristic aging process (Gordon et al. (2012) *J. Cell Biol.* 199, 9-13; Navid et al. (2012) *Bioinformation* 8, 221-224).

Children with progeria usually develop severe hardening of the arteries. This is a condition in which the walls of their arteries stiffen and thicken, often restricting blood flow. Most children with progeria die of complications related to atherosclerosis, including problems with the blood vessels that supply the heart (cardiovascular problems), resulting in heart attack and congestive heart failure, and problems with the blood vessels that supply the brain (cerebrovascular problems), resulting in stroke (Gerhard-Herman et al. (2012) *Hypertension* 59, 92-7; Low et al. (2005) *BMC Medical Genetics* 6, 38).

There are other progeroid syndromes that run in families (Navarro et al. (2006) *Hum. Mol. Genet.* 15, R151-161). They include, but are not limited to, Wiedemann-Rautenstrauch syndrome (WRS), Werner syndrome (WS), Bloom Syndrome, and Cockayne syndrome (CS). In Wiedemann-Rautenstrauch syndrome, also known as neonatal progeroid syndrome, the onset of aging begins in the womb, and signs and symptoms are already apparent at birth. Werner syndrome typically begins in adolescence or early adulthood.

These inherited progeroid syndromes also cause rapid aging and shortened life span. In the case of Werner syndrome, it has a global incidence rate of <1 in 100,000 live births, although the incidence in Japan and Sardinia is higher, where it affects ~1 in 20,000-40,000 and ~1 in 50,000, respectively. In 2006, there were ~1,300 reported cases of WS worldwide.

Hypothermia and its Relationship with Aging

In recent years, many factors have been theorized to prevent or delay the onset of diseases that affect longevity or to have a direct, independent, or multi-factor inter-related effect on increasing lifespan. Influences such as free radicals, caloric restriction, lowered body temperature, and even components in red wine (e.g., resveratrol) have each been explored.

Even when links have been suggested or established, there remains the practical issue of how to effectively achieve decreased caloric intake, free radical reduction, or the benefits of red wine, for example, without significant lifestyle modifications that must be sustained long-term at often extreme levels and with great difficulty and inconsistency in implementation.

In the case of body temperature reduction, there is presently no practical means of achieving mild and controlled hypothermia (such as a decrease from normal baseline to the range of ~95° F. to ~98° F.) that may be of clinical benefit on a chronic-use basis. In fact, studies have shown that a lower average core body temperature by ~0.2° C., which sounds like a modest reduction, is statistically significant and similar to the reduction observed in long-lived, calorie-restricted mice (Soare et al. (2011) *Aging*, 3, 374-379).

Although moderate hypothermia induction (a ~2-4° C. reduction in core temperature) has been established as having clinical benefit, for example in the prevention of organ and neurological damage post-cardiac arrest resuscitation, current methods of achieving hypothermic induction are relatively extreme acute interventions that currently can be accomplished only through the application of artificial 'forced' or external methods (e.g., cold blankets, iced saline infusion) accompanied by extreme procedures and processes that, for example, require intubation and ventilatory assistance, heavy sedation and induced paralysis simply to offset the body's natural defense of shivering in response to external attempts to reduce core body temperature.

The 'mechanical' or 'forced' methodologies in current use are clearly impractical for chronic, routine application and long-term induction of a controlled, regulated reduction in body temperature.

Much evidence of lowered core body temperature's independent effect on prolonging lifespan has emerged in recent years. These findings demonstrate the importance of a reduction of body temperature in modulating longevity.

In the case of the Scripps study, scientists lowered core body temperature directly, without restricting food intake. In cold-blooded animals, such as roundworms (*C. elegans*) and fruit flies (*Drosophila*), this task is straightforward; core body temperature can be lowered simply by changing the temperature of the environment.

However, for warm-blooded animals, the task is much more challenging. The Scripps experiment focused on the preoptic area of the hypothalamus, a structure in the brain that acts as the body's thermostat and is crucial to temperature regulation. Just as holding something warm near the thermostat in a room can fool it into thinking that the entire room is hotter so that the air conditioning turns on, the Scripps Research team reasoned that they could reset the brain's thermostat by producing heat nearby. To do so, they created a mouse model that produced large quantities of uncoupling protein 2 in hypocretin neurons in the lateral hypothalamus, near the preoptic area. The action of uncoupling protein 2 produced heat, which diffuses to other brain structures, including the preoptic area. Indeed, the extra heat worked to induce a continuous reduction of the core body temperature of the mice, lowering it from ~0.3 to ~0.5° C. The scientists were then able to measure the effect of lowered core body temperature on lifespan, finding that the mice with lowered core body temperature had significantly longer median lifespan than those that did not have a lowered core body temperature.

The researchers performed several experiments to make sure that other factors were not contributing to the lowered core body temperature. They confirmed that the experimental mice were normal in their ability to generate a fever, and that these mice moved around to about the same degree as normal mice. Additionally, the researchers verified that the hypocretin neurons producing uncoupling protein 2 were not involved in temperature regulation. Importantly, the mice in this study were allowed to eat as much food as they wished, and the experimental and control mice ate the same amount (Conti et al. (2006) *Science* 314, 825-828).

Several other studies have documented a lowering of core body temperature by caloric restriction in mice, rats, and rhesus monkeys. Interestingly, however, ad libitum-fed transgenic mice overexpressing the uncoupling protein 2 in hypocretin neurons (Hcrt-UCP2) also had a lower core body temperature and a 16% greater life expectancy than wild-type animals, independent of caloric intake.

Although body temperature is recognized as a clinically useful physiological parameter in the context of infection or extreme environmental exposures, few epidemiological studies have included body temperature as a routine measurement. One consistent observation that has emerged from studies of human body temperature, however, has been that advanced age is associated with lower body temperature.

In the landmark cross-sectional studies of Wunderlich in the 1860s—which included 25,000 participants and established the "normal" body temperature of 98.6° F.—lower body temperatures were observed in elderly participants (Mackowiak et al. (1992) *JAMA* 268, 1578-1580).

Therapeutic Hypothermia

Hypothermia, as opposed to a modest and controlled reduction in normal body temperature, is a condition in temperature-regulating organisms where the core body temperature is reduced below the normal range. Hypothermia has been used clinically for more than 40 years to protect bodily organs from various pathophysiological insults, including ischemic insults such as cardiac arrest, hemorrhage, hypergravity, and hypoglycemia, and to reduce the toxicity of various drugs and environmental toxicants (Gordon (2001) *Emerg. Med. J.* 18, 81-9).

While the precise mechanisms responsible for the therapeutic effects of hypothermia are not fully understood, hypothermia causes a general reduction in cellular metabolism (Polderman (2008) *Lancet* 371, 1955-69). This reduction during hypothermia is especially beneficial to highly aerobic organs, such as the brain and heart, under ischemic conditions because it leads to reduced demand for oxygen.

Forced hypothermic methods are used for therapeutic hypothermia. Forced hypothermia involves the use of external mechanical and/or endovascular cooling methods to extract heat from the body to reduce the body temperature below the normal temperature set point. External cooling methods include immersing a subject in a cool bath or applying blankets or pads with cooled water circulating through channels in the walls of the blanket or pad to the skin of a subject. Other external methods include wetting of the skin or hair of the subject, cooling the air around the subject, and blowing air across the subject's skin. Endovascular cooling generally involves the rapid intravenous administration of an iced saline solution or heat exchange with a specially designed catheter.

Hypothermia after Cardiac Arrest

In heart surgery, induction of hypothermia (to 28-32° C.) before cardiac arrest has been used successfully since the 1950s to protect the brain against global ischemia.

Successful use of therapeutic hypothermia after cardiac arrest in humans was also described in the late 1950s (Benson et al. (1959) *Anesth. Analg.* 38, 423-428; Williams & Spencer (1958) *Ann. Surg.* 148, 462-468; Ravitch et al. (1961) *N. Engl. J. Med.* 264, 36-38) but was subsequently abandoned because of uncertain benefit and difficulties with its use (Marion et al. (1996) *Crit. Care Med* 24, 81S-89S).

More recently, the induction of hypothermia after the return of spontaneous circulation (ROSC) has been associated with improved functional recovery and reduced cerebral histological deficits in various animal models of cardiac arrest (Horn et al. (1991) *Acta Neuropathol. (Berl).* 81, 443-449; Sterz et al. (1991) *Crit. Care Med.* 19, 379-389; D'Cruz et al. (2002) *J. Cereb. Blood Flow Metab.* 22, 848-851; Hicks et al. (2000) *J. Cereb. Blood Flow Metab.* 20, 520-530). Further preliminary human studies were conducted subsequently (Bernard et al. (1997) *Ann. Emerg. Med.* 30, 146-153, Sanada et al. (1998) *Masui.* 47, 742-745, Yanagawa et al. (1998) *Resuscitation* 39, 61-66, Nagao et al. (2000) *J. Am. Coll. Cardiol.* 36, 776-783, Zeiner et al. (2000) *Stroke* 31, 86-94, Felberg et al. (2001) *Circulation* 104, 1799-1804, Hachimi-Idrissi et al. (2001) *Resuscitation* 51, 275-281, Callaway et al. (2002) *Resuscitation* 52, 159-165).

At the time of publication of the American Heart Association/International Liaison Committee on Resuscitation (AHA/ILCOR) 2000 Guidelines for Cardiopulmonary Resuscitation and Emergency Cardiovascular Care, the evidence was insufficient to recommend use of therapeutic hypothermia after resuscitation from cardiac arrest (AHA/ILCOR (2000) *Resuscitation* 46, 1-447), but two subsequent studies, one conducted in post-cardiac arrest resuscitated patients in Australia (Bernard et al. (2002) *NEJM* 346, 557-563) and the second in post-cardiac arrest resuscitated patients conducted by the Hypothermia After Cardiac Arrest Study Group (HACA) in nine European centers (HACA (2002) *NEJM* 346, 549-556, became the basis for the AHA/ILCOR recommendation for the use of therapeutic hypothermia in the treatment of post cardiac arrest resuscitated patients issued in 2003.

Indeed, the AHA/ILCOR Recommendations, issued in June/July 2003, state that "On the basis of the published evidence to date, the ILCOR ALS Task Force has made the following recommendations:

Unconscious adult patients with spontaneous circulation after out-of-hospital cardiac arrest should be cooled to 32° C. to 34° C. for 12 to 24 hours when the initial rhythm was VF [ventricular fibrillation].

Such cooling may also be beneficial for other rhythms or in-hospital cardiac arrest."

Thus, the use of therapeutic hypothermia is now accepted as a standard intervention for the preservation of vital organ systems in the aftermath of cardiac arrest (AHA/ILCOR recommendations).

Therapeutic hypothermia can be achieved mechanically, using medical devices such as, for example, the ThermoSuit®. The ThermoSuit® cools the patient with direct water on skin contact. The water flows over the patient and is returned to the pump. A continuous flow of water is cycled through drawing heat off the body in a much more rapid process than either gel pads or cooling blankets; a treatment period of ~30 mm is usually sufficient to cause a body core temperature reduction of ~3° C. The suit is portable and is used with a conventional gurney. As the patient reaches the target temperature the water is drawn off the patient and the ThermoSuit® is removed.

While the application of therapeutic hypothermia is accepted as the standard intervention for the preservation of vital organ function in the aftermath of cardiac arrest (AHA/ILCOR recommendation), there is at present no effective pharmacological means to lower and maintain body temperature.

Chronotherapeutics

The existence of circadian rhythms in cardiovascular disease is well-established. It is also known that heart rate and blood pressure normally peak during the morning hours and reach a nadir in the late evening, around bedtime. The incidence of myocardial infarction, stroke, sudden cardiac death, and myocardial ischemia increases during the early-morning hours. Angina attacks occur in a diurnal cycle; their occurrence is common in the hours shortly after an individual begins activity, after waking. Body temperature also follows circadian patterns, where core temperature is typically lower in the morning hours and higher in the afternoon and evening hours.

Based on these relationships, researchers have begun to apply the science of chronotherapeutics, or the timing of drug effect with biologic need, to improve cardiovascular outcomes. Traditional treatment regimens for conditions associated with circadian variation typically do not account for circadian fluctuations in disease activity.

Chronotherapeutic regimens are intended to provide pharmacological intervention at the most appropriate time point(s), in accordance with circadian rhythms. The concept of chronotherapeutics in treating cardiovascular diseases includes dosing traditional agents at specific times throughout the day, the development of new agents, and the development of chronotherapeutic formulations and combinations of drugs with special release mechanisms targeted at inducing the greatest effect during the pre- and post-waking morning surge in heart rate (HR) and blood pressure (BP) and/or, in select populations, during sleep.

Chronotherapeutic agents are specifically intended to provide peak plasma concentrations when their effect is most needed (e.g., in the early morning hours with regard to HR and BP; in the case of regulating body temperature, the reverse may be true). Further, the lowest concentrations of drugs typically occur at night, when HR and BP are typically lowest and, consequently, cardiovascular events are least likely to occur. However, special consideration also needs to be given to overnight levels of the drug(s) for nocturnal hypertensives, and for all hypertensives in the pre- and post-waking hours, where HR and BP (and the calculated RPP, a measure of myocardial oxygen demand and a surrogate predictor of target organ damage and cardiovascular events) rise.

Pharmacological Means for Inducing Therapeutic Hypothermia

There is presently no effective pharmacological means to lower and maintain body temperature over a prolonged period of time. Therapeutic hypothermia is currently restricted to short-term use in acute medical situations that require the induction of mild hypothermia (body temperature in the range of ~32° C. to ~34° C.).

For example, US 2012/0282227 A1 (Katz) describes compositions and methods for inducing moderate hypothermia in a subject as an acute, short-term intravenously delivered intervention targeting a therapeutic range of between 32 and 34° C. for 12-24 h duration. However, this is not suitable for chronic, long-term application.

Such acute, mild hypothermia is distinct from modest and controlled hypothermia (a decrease from normal baseline to the range of ~95° F. to ~98° F.), which may be of clinical benefit on a chronic-use basis and does not require intravenous administration. The compositions described by Katz are reported to be useful in treating acute clinical insults, including, but not limited to, cerebral ischemic insults, such as post-cardiac arrest resuscitation neurological damage, stroke, spinal cord injury, or traumatic brain injury.

The Katz patent application (US 2012/0282227) also mentions the use of a neurotensin analog, NT69L, for inducing moderate hypothermia. Neurotensin is a 13-amino-acid neuropeptide that regulates the release of leuteinizing hormone and prolactin. An analog of neurotensin refers to a polypeptide analog of neurotensin that may have an amino acid sequence that is longer, shorter, or the same length as the amino acid sequence of neurotensin. Neurotensin analogs may include non-naturally-occurring amino acids and may also include non-amino acid compounds. However, NT69L has hypothermic tolerance issues that would prevent its chronic use.

Methods are also reported to be useful for maintaining regulated mild hypothermia in a subject for a prolonged period of time (i.e., 12-24 h or more) and for reducing the time necessary to induce regulated hypothermia, as compared to mechanical methods of induction (US 2012/0282227).

The compositions or multidrug combinations of Katz' invention comprise a regulated hypothermic compound or a dopamine receptor agonist, a vasoactive compound, and an anti-arrhythmic compound or a serotonin 5-$HT_3$ receptor antagonist.

As an example, the patent application describes
A composition comprising:
a regulated hypothermic compound or a dopamine receptor agonist,
a vasoactive compound, and
an anti-arrhythmic compound or a serotonin 5-$HT_3$ receptor antagonist.

Various combinations of drug components are described. In some examples, the compositions comprise ethanol and optionally at least one of a vasoactive compound, an anti-hyperglycemic compound, a dopamine receptor agonist, an anti-arrhythmic compound, a serotonin 5-$HT_3$ receptor antagonist, an anti-oxidant, a vitamin, and N-acetylcysteine.

In the examples where the composition or multidrug combination comprises ethanol and optionally additional agents, the method of administration requires a two-phase method of delivery of the composition. The invention described further recognizes that a two phase delivery, a delivery of a high concentration of the multidrug combination followed by delivery of a lower concentration of the multidrug combination. This two phase method of delivery may be accomplished by a rapid infusion of the composition to induce hypothermia followed by a period of slow infusion, rapidly reducing the body temperature of a patient and maintaining the hypothermic state for a sustained period of time. Using this method of delivery, the composition may comprise a regulated hypothermic compound or a dopamine receptor agonist, a vasoactive compound, and an anti-arrhythmic compound or a serotonin 5-$HT_3$ receptor antagonist and additional additives, as discussed above.

Additionally, using the two-phase method of delivery, the composition may comprise ethanol and at least one of a vasoactive compound, an anti-arrhythmic compound, a serotonin 5-$HT_3$ receptor antagonist, an anti-oxidant, a vitamin, N-acetylcysteine, and an anti-hyperglycemic compound. This two-phase delivery method can be used to deliver any of the compositions of the invention and provides significant benefits to a patient.

The methods disclosed include a method for inducing hypothermia in a subject comprising administering to the subject a multidrug combination comprising a regulated hypothermic compound or a dopamine receptor agonist, a vasoactive compound, and an anti-arrhythmic compound or a serotonin 5-$HT_3$ receptor antagonist.

In those embodiments where the clinical insult is of an acute nature, the methods were capable of preventing or limiting permanent injuries or stress, particularly if used within the first few hours after the clinical insult. The methods were reported to be useful in treating patients suffering from brain injuries, heart injuries, kidney injuries, cardiac bypass patients, patients suffering cardiac arrest, patients with neurologic injury, infants with hypoxic-ischemic encephalopathy, and injuries of vital organs related to ischemia-reperfusion. Thus, these methods can be used to reduce the stress and discomfort of shivering and to positively benefit and prevent injuries to the brain, heart, kidneys, and other organs. The methods lead to a reduction in mortality or a reduction in adverse effects attributed directly or indirectly to the clinical event.

Studies have shown that a lower average core body temperature by ~0.2° C., which is a modest reduction, is statistically significant and similar to the reduction observed in long-lived, calorie-restricted mice (see Soare et al. (2011) *Aging* 3, 374-379). In the case of body temperature reduction, there is presently no practical means of achieving and sustaining such modest and controlled hypothermia (a decrease from normal baseline to the range of ~95° F. to ~98° F.) that may be of clinical benefit on a chronic-use basis.

Thus, there is a continuing need to provide drugs or drug products that safely lower body temperature by BLSA study amounts (~95° F. to ~98° F.), suitable for chronic low-dose use.

Embodiments of the present invention address that continuing need, providing effective pharmacological means to achieve modest and controlled hypothermia (a decrease from normal baseline to the range of ~95° F. to ~98° F.).

SUMMARY OF THE INVENTION

The present invention is directed to combination pharmacological treatments that induce a prolonged modest decrease in core body temperature, into the range of ~95° F. to ~98.5° F. (~35° C. to ~36.7° C.) to mitigate and delay the early onset and progression of fatal disease processes associated with premature aging, such as those characteristic of progeria (also known as Hutchinson-Gilford Progeria Syndrome or HGPS), Wiedemann-Rautenstrauch syndrome (also known as neonatal progeroid syndrome), Werner syndrome, and other rare disorders characterized by premature aging, and to prolong the shortened lifespan of children afflicted with these diseases.

Short-term chronic administration of the pharmaceutical treatment to a person suffering from mild concussion (e.g., sports-related injury, automobile accident, falls, bumps) may also have value in ameliorating the neurological damage/symptoms associated with mild concussion where a modest decrease in body temperature for a prescribed number of days or short course of treatment could minimize damage and potentially hasten recovery time.

Chronic administration of the pharmacological treatment may also have value in normal human populations or in high-risk human populations, such as those with a family history of heart disease or cancer or in patients with compromised cardiac status or organ damage, by delaying or preventing the onset and progression of potentially fatal, life-shortening disease processes and prolonging the potentially shortened lifespan of at-risk patients or the potential life span of human populations, whether or not at risk. Similar benefits may be realized in other mammal populations, such as canines, felines, and other non-human species.

The present invention is directed to drugs or drug products, including, but not limited to, combinations of drugs, that safely lower body temperature by BLSA study-like amounts (lower $50^{th}$ percentile), suitable for chronic low-dose use, providing an effective method to achieve modest and controlled hypothermia (a decrease from normal baseline into the range of ~95° F. to ~98° F.).

The focus of the present invention is on the pharmacological induction of prolonged modestly reduced body temperature (in the range of ~95° F. to ~98° F.) to achieve the presumed organ protective and resulting lifespan-extending effects of hypothermia.

Embodiments of the invention include unique combination drug formulations (two or more medications in one drug product) at doses lower than those normally used in monotherapy with the drugs in question.

Embodiments of the invention include unique combination drug formulations (two or more pharmaceutical agents in one drug product) at doses similar to those normally used in monotherapy with the drugs in question.

Embodiments of the invention include unique combination drug formulations (two or more pharmaceutical agents in one drug product) at doses higher than those normally used in monotherapy with the drugs in question.

Embodiments of the invention include combination drug products formulated as time-release or extended-release products.

Similar to the discussion above on cardiovascular disease, circadian fluctuations in disease activity, and chronotherapeutics, there is some evidence, for example, that olanzapine may be optimally effective in the 'dark period' with respect to temperature decrease. Metformin may be ideally suited for its desired effects occurring in the 'light period.' Thus, embodiments of the present invention include chronotherapeutic formulations of drugs or drug products, including combinations of drugs, that safely lower body temperature by BLSA study-like amounts (lower $50^{th}$ percentile), suitable for chronic low-dose use, providing effective pharmacological methods to achieve modest and controlled hypothermia (a decrease from normal baseline into the range of ~95° F. to ~98° F.).

Embodiments of the invention include combination drug products formulated as chronotherapeutic products.

Embodiments of the invention include a pharmaceutical composition and method of treatment where the combination pharmaceutical entity containing prescribed doses of an atypical anti-psychotic drug with hypothermia-inducing properties, such as olanzapine (Evers and Scheurink, Dutch Research Consortium, 2011) or risperidone (Cope et al. (2009) *Physiol. Behav.* 96, 457-463), or an indole alkaloid anti-psychotic and anti-hypertensive drug, such as reserpine, and an oral anti-diabetic drug in the biguanide class, such as metformin (Wu et al. (2008) *JAMA* 299, 185-93)), which has caloric-restriction and other desired effects, such as weight loss, reduced insulin resistance, and increased metabolism (e.g., Ji et al. (2013) *PloS One* 8, e57222), to balance or offset the potential for weight gain, decreased metabolism, and increased insulin resistance associated with atypical anti-psychotics, or similarly, an anti-inflammatory, anti-allergic immunomodulator, such as amlexanox, that has been shown to reverse obesity, diabetes, and fatty liver in mice (Reilly et al. 2013 Nat. Med. 19, 313-321), administered orally, for example, in the form of a pill, gel-cap, liquid, cream, or spray form.

While the primary indication for use of atypical anti-psychotics is the treatment of schizophrenia, drugs in this class have a documented history of off-label use to treat anxiety disorder, attention deficit hyperactivity disorder, dementia and severe geriatric agitation, major depressive disorder, eating disorders, insomnia, obsessive compulsive disorder (OCD), post-traumatic stress disorder (PTSD), personality disorders, substance abuse, and Tourette's syndrome (Maglione et al., Off-label Use of Atypical Anti-psychotics, Comparative Effectiveness Reviews, No. 43, Agency for Healthcare Research and Quality (US), DHHS, Report No.: 11-EHC087-EF, September 2011), and that in the normal course of development of all FDA approved drugs, including atypical anti-psychotics such as olanzapine, safety trials in healthy normal human subject volunteers are also required, and this has been the case for all previously approved subject drugs referenced here. While not approved for a specific indication other than schizophrenia, the use of these drugs in normal volunteers under strict regulatory scrutiny is well-established. Relative to the current application, it should be noted that the use of approved drugs to elicit a potentially positive 'side effect' and apply it for that purpose to the treatment of a secondary medical indication distinct from the approved use (repurposing) is not unprecedented. In a classic example, minoxidil, an approved anti-hypertensive, was repurposed for the treatment of male pattern baldness and alopecia on the basis of an observation of an incidental minoxidil side-effect, hair growth, which resulted in development of the topical form of minoxidil, known as Rogaine®.

While a modest, sustained decrease in body temperature is the focus of the current invention, and the primary purpose of the inclusion of metformin is to offset the potential negative effects of the hypothermia-inducing drug component, metformin may have complementary independent properties that may expand or enhance the value of the desired effect of the combination. For example, Mayo Clinic researchers found that women with ovarian cancer who took metformin were, on average, nearly four times more likely to survive for 5 years after diagnosis than women not taking the drug (Kumar et al. (2013) Cancer 119, 555-562). Other studies suggest that metformin helps slow or stop tumor growth in other cancers too (Hassan et al. (2010) Cancer 116, 1938-1946; Yang (2011) Front. Med. 5, 115-117; Kirpichnikov et al. (2002) Ann Intern Med. 137, 25-33). To further support that metformin may have complementary independent properties that may supplement or enhance the primary body temperature lowering focus of the invention, there is growing evidence that metformin reduces the risk of cardiovascular disease. For example, it was reported by Dr. Peter Boyle (International Prevention Research Institute, Lyon, France) that in 29 different studies, metformin was associated with a 10% reduction in the risk of cardiovascular events, with the drug associated with a 10% reduction in the risk of heart failure in seven studies and a 12% reduction in the risk of MI in nine studies (Boyle, P. et al. Safety of glucose-lowering medications: The Diabetes Adverse Event Monitor (DIABAMON) project: II cardiovascular disease. American Diabetes Association 2013 Scientific sessions; Jun. 23, 2013; Chicago, Ill. Abstract 1405-P).

In a preferred embodiment, the pharmaceutical composition is administered to children afflicted with progeria or other diseases characterized by premature aging and shortened life spans, as a means to slow the onset and progression of associated age-related diseases and effectively extend the expected lifespan.

In a preferred embodiment, the pharmaceutical composition is administered to a person suffering from mild-to-moderate concussion, to ameliorate the neurological damage/symptoms associated with concussion (e.g., sports-related injury, minor automobile accident, falls, bumps) where a modest decrease in body temperature for a prescribed number of days or short course of treatment could minimize damage and potentially hasten recovery time.

In a preferred embodiment, the pharmaceutical composition is administered to a person with the intent to prolong longevity.

In a preferred embodiment, the pharmaceutical composition is administered to a menopausal female to alleviate, reduce the occurrence of or minimize the effect of hot flashes.

In a preferred embodiment, the olanzapine or risperidone or reserpine component of the combination exerts a body temperature-lowering effect.

Embodiments of the invention include pharmaceutical combinations of olanzapine or risperidone or reserpine with metformin.

Embodiments of the invention include pharmaceutical combinations of olanzapine or risperidone or reserpine with amlexanox.

Embodiments of the combination drug invention may include a pharmaceutical component with temperature reduction properties, such as a neurotensin analog, such as T69L (Katz patent application US 2012/0282227) or similar analogs, in combination with, for example, metformin or amlexanox.

Embodiments of the combination drug invention may include a pharmaceutical component with body temperature-reducing properties such as β-blockers, clonidine, ethanol, phenothiazines, neuroleptics and sedative hypnotics, with metformin or amlexanox.

BRIEF DESCRIPTION OF THE FIGURES

Correlations between longevity and three factors—body temperature, insulin levels, and DHEAS levels—were found both in monkey studies and in the Baltimore Longitudinal Study of Aging (BLSA). The figure summarizes these findings. For male rhesus monkeys, it graphs the effects of caloric restriction versus control monkeys who were not calorie-restricted (parts A, B, and C). For men in the BLSA, it shows the effects of the same three factors on natural longevity, expressed in terms of survival time (parts D, E, and F). Men who had lower body temperatures and lower insulin levels—although they were not calorically restricted, as the rhesus monkeys were—lived longer (top survival curves in the graphs) than those who had higher values in those parameters (bottom survival curves). Source: Roth et al. (2002) Science 297, 811.

Mice were fed ad libitum on sterilized breeder chow. Median life span was (A) 20% (females) and (C) 12% (males) greater in Hcrt-UCP2 mice relative to wild-type littermates. Complementary logarithmic plots (B and D) suggest that the ratio of the hazard rates for Hcrt-UCP2 and wild-type littermates was approximately constant with time. This assessment was verified by testing the significance of age as a time-dependent covariate. tg, transgenic; wt, wild-type. Source: Conti et al. (2006) Science 314, 825-828.

Source: Waalen & Buxbaum (2011) J. Gerontol. A Biol. Sci. Med. Sci. 66A, 487-492.

DETAILED DESCRIPTION OF THE INVENTION

As stated above, and described in detail below, the present invention is directed to drugs or drug products, providing effective pharmacological means to achieve modest and controlled hypothermia (a decrease from normal baseline to the range of ~95° F. to ~98° F.).

The present invention is directed to combination pharmacological treatments that induce a prolonged modest decrease in core body temperature, into the range of ~95° F. to ~98.5° F. (~35° C. to ~36.7° C.), to mitigate and delay the early onset and progression of fatal disease processes associated with premature aging, such as those characteristic of progeria (also known as Hutchinson-Gilford Progeria Syndrome or HGPS), Wiedemann-Rautenstrauch syndrome (also known as neonatal progeroid syndrome), Werner syndrome, and other rare disorders characterized by premature aging, and to prolong the shortened lifespan of children afflicted with these diseases.

Short-term chronic administration of the pharmaceutical treatment to a person suffering from mild concussion (e.g., sports-related injury, automobile accident, falls, bumps) may also have value in ameliorating the neurological damage/ symptoms associated with mild concussion, where a modest decrease in body temperature for a prescribed number of days or short course of treatment could minimize damage and potentially hasten recovery time.

Chronic administration of the pharmacological treatment may also have value in normal human populations or in high-risk human populations, such as those with a family history of heart disease or cancer or in patients with compromised cardiac status or organ damage, by delaying or preventing the onset and progression of potentially fatal, life-shortening disease processes and prolonging the potentially shortened lifespan of at-risk patients or the potential life span of human populations, whether or not at risk. Similar benefits may be realized in other mammalian populations such as canines, felines, and other non-human species.

The present invention is directed to drugs or drug products, including combinations of drugs, that safely lower body temperature by BLSA study-like amounts (lower $50^{th}$ percentile), suitable for chronic low-dose use, providing effective pharmacological means to achieve mild and controlled hypothermia (a decrease from normal baseline to the range of ~95° F. to ~98° F.).

The focus of the present invention is on the pharmacological induction of prolonged, modestly reduced body temperature (in the range of ~95° F. to ~98° F.) to achieve the presumed organ-protective and resulting lifespan-extending effects of hypothermia.

Embodiments of the invention include unique combination drug formulations (two or more medications in one drug product) at doses lower than those normally used in monotherapy with the drugs in question.

Embodiments of the invention include unique combination drug formulations (two or more medications in one drug product) at doses similar to those normally used in monotherapy with the drugs in question.

Embodiments of the invention include unique combination drug formulations (two or more medications in one drug product) at doses higher than those normally used in monotherapy with the drugs in question.

Embodiments of the invention include combination drug products formulated as time-release or extended-release products.

Embodiments of the invention include combination drug products formulated as chronotherapeutic products.

Embodiments of the invention include a pharmaceutical composition and method of treatment where the combination pharmaceutical entity containing prescribed doses of an atypical anti-psychotic drug with hypothermia-inducing properties, such as olanzapine (Evers and Scheurink, Dutch Research Consortium, 2011) or risperidone (Cope et al. (2009) *Physiol. Behav.* 96, 457-463), or an indole alkaloid anti-psychotic and anti-hypertensive drug, such as reserpine, and an oral anti-diabetic drug in the biguanide class, such as metformin (Wu et al. (2008) *JAMA* 299, 185-93)), which has caloric-restriction and other desired effects, such as weight loss, reduced insulin resistance, and increased metabolism (e.g., Ji et al. (2013) *PloS One* 8, e57222), to balance or offset the potential for weight gain, decreased metabolism, and increased insulin resistance associated with atypical anti-psychotics, or similarly, an anti-inflammatory, anti-allergic immunomodulatory drug, such as amlexanox, that has been shown to reverse obesity, diabetes, and fatty liver in mice (Reilly et al. (2013) *Nat. Med.* 19, 313-321), administered orally, for example, in the form of a pill or in liquid or spray form, or as a drug-impregnated patch.

In a preferred embodiment, the pharmaceutical composition is administered to children afflicted with progeria or other diseases characterized by premature aging and shortened life span.

In a preferred embodiment, the pharmaceutical composition is administered to a person suffering from concussion, to ameliorate the neurological damage/symptoms associated with concussion (e.g., sports-related injuries, automobile accidents, falls, bumps).

In a preferred embodiment, the pharmaceutical composition is administered to a person suffering from or at risk of developing cardiac disease, such as atherosclerotic disease, stroke, or having a family history of cardiac disease, to delay the onset, progression, or severity of the disease process(es).

In a preferred embodiment, the pharmaceutical composition is administered to a person suffering from or at risk of developing organ damage, such as kidney disease or liver disease, to delay the onset, progression, or severity of the disease process(es).

In a preferred embodiment, the pharmaceutical composition is administered to a person pre- and post-organ transplant to optimize transplant success and avoid post-transplant complications associated with, for example, rejection and organ failure.

In a preferred embodiment, pharmaceutical composition is administered to an organ donor to preserve the organs before harvesting for transplant.

In a preferred embodiment, the pharmaceutical composition is administered on a chronic basis to a normal or at-risk person for the purpose of extending, prolonging, or maximizing lifespan potential.

In a preferred embodiment, the pharmaceutical composition is administered on a chronic basis to canines, felines, and other non-human mammal species for the purpose of extending, prolonging, or maximizing lifespan.

In a preferred embodiment, the olanzapine, risperidone, or reserpine component of the combination exerts a body temperature-lowering effect.

Embodiments of the invention include pharmaceutical combinations of olanzapine, risperidone, or reserpine with metformin.

Embodiments of the invention include pharmaceutical combinations of olanzapine, risperidone, or reserpine with amlexanox.

Embodiments of the combination drug invention may include a pharmaceutical component with temperature-reducing properties, such as a neurotensin analog, such as NT69L (Katz patent application US 2012/0282227) or similar analogs, in combination with, for example, metformin or amlexanox.

Embodiments of the combination drug invention may include a pharmaceutical component with body temperature-reducing properties, such as β-blockers, clonidine, ethanol, phenothiazines, neuroleptics, and sedative hypnotics, with metformin or amlexanox.

EXAMPLES

Pharmaceutical Compositions

Pharmaceutical compositions of the present disclosure comprise at least one compound, or tautomer, stereoisomer, pharmaceutically acceptable salt or hydrate thereof, formulated together with one or more pharmaceutically acceptable carriers. These formulations include those suitable for oral, rectal, topical (e.g., drug-impregnated patch), buccal, and parenteral (e.g., subcutaneous, intramuscular, intradermal, or intravenous) administration. The most suitable form of administration in any given case will depend on the degree and severity of the condition being treated and on the nature of the particular compound being used.

Formulations suitable for oral administration may be presented in discrete units, such as capsules, cachets, lozenges, tablets, or patches, each containing a predetermined amount of a compound of the present disclosure as powder or granules; as a solution or a suspension in an aqueous or non-aqueous liquid; or as an oil-in-water or water-in-oil emulsion. As indicated, such formulations may be prepared by any suitable method of pharmacy which includes the step of bringing into association at least one compound of the present disclosure as the active compound and a carrier or excipient (which may constitute one or more accessory ingredients). The carrier must be acceptable in the sense of being compatible with the other ingredients of the formulation and must not be deleterious to the recipient. The carrier may be a solid or a liquid, or both, and may be formulated with at least one compound described herein as the active compound in a unit-dose formulation, for example, a tablet, which may contain from ~0.05% to ~95% by weight of the at least one active compound. Other pharmacologically active substances may also be present including other compounds. The formulations of the present disclosure may be prepared by any of the well-known techniques of pharmacy consisting essentially of admixing the components.

For solid compositions, conventional non-toxic solid carriers include, for example, pharmaceutical grades of mannitol, lactose, starch, magnesium stearate, sodium saccharin, talc, cellulose, glucose, sucrose, magnesium carbonate, and the like. Liquid pharmacologically administrable compositions can, for example, be prepared by dissolving or dispersing, at least one active compound of the present disclosure as described here and optional pharmaceutical adjuvants in an excipient, such as, for example, water, saline, aqueous dextrose, glycerol, ethanol, and the like, to thereby form a solution, ointment, or suspension. Generally, suitable formulations may be prepared by uniformly and intimately admixing at least one active compound of the present disclosure with a liquid or finely divided solid carrier, or both, and then, if necessary, shaping the product. For example, a tablet may be prepared by compressing or molding a powder or granules of at least one compound of the present disclosure, which may be optionally combined with one or more accessory ingredients. Compressed tablets may be prepared by compressing, in a suitable machine, at least one compound of the present disclosure in a free-flowing form, such as a powder or granules, which may be optionally mixed with a binder, lubricant, inert diluent and/or surface active/dispersing agent(s). Molded tablets may be made by molding, in a suitable machine, where the powdered form of at least one compound of the present disclosure is moistened with an inert liquid diluent.

Formulations suitable for buccal (sub-lingual) administration include lozenges comprising at least one compound of the present disclosure in a flavored base, usually sucrose and acacia or tragacanth, and pastilles comprising the at least one compound in an inert base such as gelatin and glycerin or sucrose and acacia.

Formulations of the present disclosure suitable for parenteral administration comprise sterile aqueous preparations of at least one compound or tautomers, stereoisomers, pharmaceutically acceptable salts, and hydrates thereof, which are approximately isotonic with the blood of the intended recipient. These preparations are administered intravenously, although administration may also be effected by means of subcutaneous, intramuscular, or intradermal injection. Such preparations may conveniently be prepared by admixing at least one compound described herein with water and rendering the resulting solution sterile and isotonic with the blood. Injectable compositions according to the present disclosure may contain from ~0.1 to ~5% (w/w) of the active compound.

Formulations suitable for rectal administration are presented as unit-dose suppositories. These may be prepared by admixing at least one compound as described herein with one or more conventional solid carriers, for example, cocoa butter, and then shaping the resulting mixture.

Formulations suitable for topical application to the skin may take the form of an ointment, cream, lotion, paste, gel, spray, aerosol, patch, or oil. Carriers and excipients that may be used include Vaseline®, lanoline, polyethylene glycols, alcohols, and combinations of two or more thereof. The active compounds are generally present at a concentration of from ~0.1% to ~15% w/w of the composition, for example, from ~0.5 to ~2%.

The amount of active compound administered may be dependent on the subject being treated, the subject's weight, the manner of administration and the judgment of the prescribing physician. For example, a dosing schedule may involve the daily or semi-daily administration of the encapsulated compound at a perceived dosage of ~4 µg to ~1000 mg. In another embodiment, intermittent administration, such as on a monthly or yearly basis, of a dose of the encapsulated compound may be employed. Encapsulation facilitates access to the site of action and allows the administration of the active ingredients simultaneously, in theory producing a synergistic effect. In accordance with standard dosing regimens, physicians will readily determine optimum dosages and will be able to readily modify administration to achieve such dosages.

A therapeutically effective amount of a compound or composition disclosed herein can be measured by the therapeutic effectiveness of the compound. The dosages, however, may be varied depending upon the requirements of the patient, the severity of the condition being treated, and the compound being used. In one embodiment, the therapeutically effective amount of a disclosed compound is sufficient to establish a maximal plasma concentration. Preliminary doses as, for example, determined according to animal tests, and the scaling of dosages for human administration is performed according to art-accepted practices.

Toxicity and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compositions that exhibit large therapeutic indices are preferable.

Data obtained from the cell culture assays or animal studies can be used in formulating a range of dosage for use in humans. Therapeutically effective dosages achieved in one animal model may be converted for use in another animal, including humans, using conversion factors known in the art (see, e.g., Freireich et al., *Cancer Chemother. Reports* 50(4):219-244 (1966) and the following Table for Equivalent Surface Area Dosage Factors).

Approximate Equivalent Surface Area Dosage Factors

| From: | To: | | | | |
|---|---|---|---|---|---|
| | Mouse (20 g) | Rat (150 g) | Monkey (3.5 kg) | Dog (8 kg) | Human (60 kg) |
| Mouse | 1 | ½ | ¼ | ⅙ | 1/12 |
| Rat | 2 | 1 | 1/12 | ¼ | 1/7 |
| Monkey | 4 | 2 | 1 | ⅗ | ⅓ |
| Dog | 6 | 4 | ⅗ | 1 | 1/12 |
| Human | 12 | 7 | 3 | 2 | 1 |

The dosage of such compounds lies preferably within a range of circulating concentrations that include the $ED_{50}$ with little or no toxicity. The dosage may vary within this range depending upon the dosage form employed and the route of administration utilized. Generally, a therapeutically effective amount may vary with the subject's age, condition, and gender, as well as the severity of the medical condition in the subject. The dosage may be determined by a physician and adjusted, as necessary, to suit observed effects of the treatment.

Example 1

Mouse or Rat Experiments

Dose-ranging experiments of various combinations of the combination drug embodiment components are conducted to establish induction, range, and maintenance of decreased body temperature in a healthy mouse or rat model.

In preliminary experiments, olanzapine, risperidone, and reserpine are evaluated independently at varying dose levels to determine the range of body temperature drop in mice or rats.

Such tests may also examine administration during the day versus evening dosing to assess potential diurnal variation in body temperature. There is some evidence, for example, that olanzapine may be optimally effective in the 'dark period' with respect to temperature decrease. Metformin may be ideally suited for its desired effects occurring in the 'light period.'

Thus, combination testing is conducted to evaluate metformin with at least one of olanzapine and risperidone and reserpine in 'morning' or 'evening' combinations or with separate components being administered in the morning and evening; for example, metformin in the morning and olanzapine in the evening, and assessing a single combination chronotherapeutic formulation with delayed release of one component to maximize diurnal characteristics/benefits of each drug's desired effect.

Example 2

Mouse or Rat Experiments

Separate 2-week dose-ranging and pharmacodynamic validation studies of three different drugs known to have temperature-lowering properties (olanzapine, risperidone, reserpine) are conducted in mice or rats to evaluate the optimal temperature-lowering pharmacodynamic effect and dose of each.

Of the three different drug candidates, two atypical anti-psychotic drugs olanzapine and risperidone, and an indole alkaloid anti-psychotic and anti-hypertensive drug, reserpine, one is selected at these experiments for subsequent evaluation in combination with metformin, an oral anti-diabetic drug of the biguanide class.

As explained previously, metformin has caloric-restriction and other desired effects, such as weight loss, reduced insulin resistance, and increased metabolism to balance or offset the potential for weight gain, decreased metabolism, and increased insulin resistance associated with anti-psychotics.

Each of the three drugs is first tested at doses at or near the equivalent therapeutic dose level for their approved indications (i.e., translational equivalent mouse or rat dose as derived/calculated from known human dosing) followed by doses at one-half the translational therapeutic dose levels, followed by translational doses higher or lower than one-half the therapeutic dose, depending on outcome evaluations at each level of testing. Parameters to be evaluated are as follows.

Primary objectives include:
Drop in temperature (actual and average/mean over time).
Sustainability of drop in temperature over time.
Intra-animal pattern of temperature drop.
Secondary objectives include:
Weight gain or loss.
Appetite.
Activity level.
Blood glucose levels.
Sleep efficacy Example 3

Mouse or Rat Experiments

Based on an outcome evaluation of the Examples 1-2 experiments, one of the three drugs (and possibly an alternate) is designated as the candidate(s) for the next stage, for evaluation as the temperature-reducing component of a combination drug product.

In this example, the selected drug(s) and dose(s) for temperature-lowering effect are evaluated when the drug is administered in the morning or in the evening or as half-doses split between morning and evening.

Evaluation objectives are the same as those in Example 2, plus an evaluation of the temperature effect in the light and dark periods (i.e., a daytime and/or nighttime effect, regardless of when the drug(s) is(are) administered).

The combination with the most desirable overall profile is then selected as the temperature-lowering component of the combination drug candidate for further evaluation.

Example 4

Mouse or Rat Experiments

The selected temperature-lowering (anti-psychotic) drug candidate at the optimal dose level is combined with three different doses of metformin at dose regimens and/or other combination permutations based on prior results that may include one or more of the following:
Combination is dosed in the morning.
Combination is dosed in the evening.
Combination is split for morning and evening dosing.
Split drug-release regimens specific to diurnal variability (a chronotherapeutic approach).
Other permutations as dictated by analyses of prior results.
Results of these are evaluated according to the objectives in Example 1, with particular emphasis on the offsetting impact of metformin on the undesired side effects of the temperature-lowering component of the combination (the anti-psychotic).

Example 5

Non-Human Mammalian Progeria Model (e.g., Mouse or Rat)

The preferred combination drug is assessed, for example, in a mouse progeria model. An established progeria mouse model experiment is used to evaluate the effect of various combinations of the proposed combination drug embodiment on lifespan in the progeria mouse (primary endpoint) with secondary evaluations of weight and general health, as well as necroscopy to evaluate the presence or stage of cardiovascular disease, cerebral/neurological changes, stroke, tumors/cancer, organ function.

Example 6

Rat Concussion Model

The preferred combination drug embodiment is assessed in an established experimental model, such as the Wistar rat concussion model developed by Viano et al. (2012) (also known as the National Football League Model; *Ann. Biomed. Eng.* 40, 213-226). The study measures (comparative evaluations) parameters such as time to recovery, quality of recovery, extent of neurological damage, post-concussion sequelae presence and duration.

Example 7

Mouse or Rat Longevity Model

The preferred combination drug embodiment is assessed in a study similar in design to the Scripps study referenced earlier (Conti et al. (2006) *Science* 314, 825-828), to evaluate lifespan outcomes in treated and non-treated animals.

Embodiments of the present invention include at least the following:

A method for the pharmacological induction of a prolonged modestly reduced body temperature (in the range of ~95° F. to ~98° F.) in a patient in need thereof.

A pharmaceutical composition comprising olanzapine and metformin that reduces the body temperature (to the range of ~95° F. to ~98° F.) of a human patient in need thereof.

A chronotherapeutic pharmaceutical formulation comprising olanzapine and metformin that safely lowers body temperature by BLSA study-like amounts (lower $50^{th}$ percentile), suitable for chronic low-dose use, providing effective pharmacological means to achieve modest and controlled hypothermia (a decrease from normal baseline to the range of ~95° F. to ~98° F.).

A pharmaceutical composition comprising doses of an atypical anti-psychotic drug with modest hypothermia-inducing properties, such as olanzapine or risperidone or an indole alkaloid anti-psychotic and anti-hypertensive drug, such as reserpine, and an oral anti-diabetic drug in the biguanide class, such as metformin.

A pharmaceutical composition comprising doses of an atypical anti-psychotic drug with modest hypothermia-inducing properties, such as olanzapine or risperidone or an indole alkaloid anti-psychotic and anti-hypertensive drug, such as reserpine, and an anti-inflammatory, anti-allergic immunomodulatory drug, such as amlexanox.

A method of treating progeria by administering a pharmaceutical composition comprising olanzapine and metformin.

TABLE 1

Experiments

| Experimental Stage | Drugs Evaluated | Doses Evaluated | Evaluation Period | Primary Outcome Measures | Secondary Outcome Measures | Overall Objective |
|---|---|---|---|---|---|---|
| One* | olanzapine risperidone reserpine | Therapeutic dose, ½ therapeutic dose, higher or lower than ½ therapeutic dose for each drug. PD and dose-ranging design. Mouse or rat. | 2 weeks per drug per dose | Drop in temp (actual and mean) Sustainability & pattern | weight gain or loss appetite activity level blood glucose levels | Select one drug to advance to stage 2 |
| Two* | Selected candidate | Mouse or rat full dose morning; full dose Half-doses split between morning & evening Mouse or rat. | 2 weeks per Regimen | As above, plus light/dark period effect | Same as stage 1 | Select optimal dosing pattern |
| Three | Selected candidate plus metformin Mouse or rat | Three different metformin doses in combination with selected candidate. Possible regimens: Morning dosing; evening dosing; split am/pm; chronotherapeutic dosing (TBD); other as dictated by prior results. | 2 weeks per Regimen | Same as Stages One and Two | Same as stage 1 | Proof-of concept, selection of preferred embodiment drug in support of IP claims |
| Four A | Preferred combination drug embodiment | Mouse or rat progeria model | TBD | Effect on lifespan | Organ damage; cardio disease progression | Indication-specific proof-of-concept |
| Four B | Preferred combination drug embodiment | Wistar rat concussion model (NFL) | TBD | Time to recovery | Comparative extent of neurological damage; quality of recovery; post-concussion sequelae presence and duration | Indication-specific proof-of-concept |
| Four C | Combination drug | Mouse or rat longevity model | TBD | Longevity | General health comparison | Indication POC |

A method of treating progeria by administering a pharmaceutical composition comprising risperidone and metformin.

A method of treating concussion using a pharmaceutical composition comprising reserpine and metformin.

A pharmaceutical composition comprising olanzapine, risperidone, or reserpine with metformin.

A pharmaceutical composition comprising olanzapine, risperidone, or reserpine with amlexanox.

A pharmaceutical composition comprising a neurotensin analog, such as NT69L, with metformin.

A pharmaceutical composition comprising a neurotensin analog, such as NT69L, with amlexanox.

A pharmaceutical composition comprising NT69L and metformin.

A pharmaceutical composition comprising NT69L and amlexanox.

A pharmaceutical composition comprising one component selected from the group consisting of β-blockers, clonidine, ethanol, phenothiazines, neuroleptics, and sedative hypnotics, with metformin.

A pharmaceutical composition comprising one component selected from the group consisting of β-blockers, clonidine, ethanol, phenothiazines, neuroleptics, and sedative hypnotics, with amlexanox.

A method for the pharmacological induction of a prolonged, modestly reduced body temperature (in the range of ~95° F. to ~98° F.) in a patient in need thereof.

A method for the pharmacological induction of a prolonged, modestly reduced body temperature (in the range of ~95° F. to ~98° F.) in a patient in need thereof comprising administering a pharmaceutical composition comprising metformin and a second agent, selected from the group consisting of olanzapine, risperidone, and reserpine.

A method for the pharmacological induction of a prolonged, modestly reduced body temperature (in the range of ~95° F. to ~98° F.) in a patient in need thereof comprising administering a pharmaceutical composition comprising metformin and olanzapine.

A method for the pharmacological induction of a prolonged, modestly reduced body temperature (in the range of ~95° F. to ~98° F.) in a patient in need thereof comprising administering a pharmaceutical composition comprising metformin and risperidone.

A method for the pharmacological induction of a prolonged, modestly reduced body temperature (in the range of ~95° F. to ~98° F.) in a patient in need thereof comprising administering a pharmaceutical composition comprising metformin and reserpine.

A pharmaceutical composition that reduces the body temperature (to the range of ~95° F. to ~98° F.) of a patient in need thereof.

A pharmaceutical composition that reduces the body temperature (to the range of ~95° F. to ~98° F.) of a patient in need thereof comprising doses of an atypical anti-psychotic drug or an indole alkaloid anti-psychotic and anti-hypertensive drug, and an oral anti-diabetic biguanide drug.

A pharmaceutical composition that reduces the body temperature (to the range of ~95° F. to ~98° F.) of a patient in need thereof comprising doses of an atypical anti-psychotic drug or an indole alkaloid anti-psychotic and anti-hypertensive drug, and an anti-inflammatory, anti-allergic immunomodulatory drug.

A pharmaceutical composition that reduces the body temperature (to the range of ~95° F. to ~98° F.) of a patient in need thereof comprising metformin and a second agent, selected from the group consisting of olanzapine, risperidone, reserpine, and a neurotensin analog.

A pharmaceutical composition that reduces the body temperature (to the range of ~95° F. to ~98° F.) of a patient in need thereof comprising amlexanox and a second agent, selected from the group consisting of olanzapine, risperidone, reserpine, and a neurotensin analog.

A pharmaceutical composition that reduces the body temperature (to the range of ~95° F. to ~98° F.) of a patient in need thereof comprising metformin and NT69L.

A pharmaceutical composition that reduces the body temperature (to the range of ~95° F. to ~98° F.) of a patient in need thereof comprising amlexanox and NT69L.

A pharmaceutical composition that reduces the body temperature (to the range of ~95° F. to ~98° F.) of a patient in need thereof comprising metformin and a second agent, selected from the group consisting of β-blockers, clonidine, ethanol, phenothiazines, neuroleptics, and sedative hypnotics.

A pharmaceutical composition that reduces the body temperature (to the range of ~95° F. to ~98° F.) of a patient in need thereof comprising amlexanox and a second agent, selected from the group consisting of β-blockers, clonidine, ethanol, phenothiazines, neuroleptics, and sedative hypnotics.

A chronotherapeutic pharmaceutical formulation that reduces the body temperature (to the range of ~95° F. to ~98° F.) of a patient in need thereof.

A chronotherapeutic pharmaceutical formulation that reduces the body temperature (to the range of ~95° F. to ~98° F.) of a patient in need thereof comprising doses of an atypical anti-psychotic drug or an indole alkaloid anti-psychotic and anti-hypertensive drug, and an oral anti-diabetic biguanide drug.

A chronotherapeutic pharmaceutical formulation that reduces the body temperature (to the range of ~95° F. to ~98° F.) of a patient in need thereof comprising doses of an atypical anti-psychotic drug or an indole alkaloid anti-psychotic and anti-hypertensive drug, and an anti-inflammatory, anti-allergic immunomodulatory drug.

A chronotherapeutic pharmaceutical formulation that reduces the body temperature (to the range of ~95° F. to ~98° F.) of a patient in need thereof comprising metformin and a second agent, selected from the group consisting of β-blockers, clonidine, ethanol, phenothiazines, neuroleptics, and sedative hypnotics, with metformin.

A chronotherapeutic pharmaceutical formulation that reduces the body temperature (to the range of ~95° F. to ~98° F.) of a patient in need thereof comprising metformin and a second agent, selected from the group consisting of olanzapine, risperidone, reserpine, and a neurotensin analog.

A chronotherapeutic pharmaceutical formulation that reduces the body temperature (to the range of ~95° F. to ~98° F.) of a patient in need thereof comprising amlexanox and a second agent, selected from the group consisting of olanzapine, risperidone, reserpine, and a neurotensin analog.

All documents, publication, manuals, article, patents, summaries, references, and other materials cited here are incorporated by reference in their entirety. Other embodiments of the invention will be apparent to those skilled in the art from consideration of the specification and practice of the invention disclosed here. It is intended that the specification and examples be considered as exemplary, with the true scope and spirit of the invention indicated by the claims.

What is claimed is:

1. A method of treating progeria in a patient in need thereof, said method comprising administering a pharmaceutical composition comprising metformin and olanzapine.

2. The method of claim 1, wherein said metformin and said olanzapine are administered concurrently.

3. The method of claim 1, comprising administering either:
   a) metformin in the morning and olanzapine in the evening; or
   b) olanzapine in the morning and metformin in the evening.

4. A method of treating Wiedemann-Rautenstrauch syndrome (WRS) in a patient in need thereof, said method comprising administering a pharmaceutical composition comprising metformin and olanzapine.

5. The method of claim 4, wherein said metformin and said olanzapine are administered concurrently.

6. The method of claim 4, comprising administering either:
   a) metformin in the morning and olanzapine in the evening; or
   b) olanzapine in the morning and metformin in the evening.

7. A method of treating Werner syndrome (WS) in a patient in need thereof, said method comprising administering a pharmaceutical composition comprising metformin and olanzapine.

8. The method of claim 7, wherein said metformin and said olanzapine are administered concurrently.

9. The method of claim 7, comprising administering either:
   a) metformin in the morning and olanzapine in the evening; or
   b) olanzapine in the morning and metformin in the evening.

* * * * *